US009511023B2

United States Patent
Hacher et al.

(10) Patent No.: US 9,511,023 B2
(45) Date of Patent: Dec. 6, 2016

(54) CLAY COMPOSITIONS

(75) Inventors: Béatrice Hacher, Angerville La Campagne (FR); Didier Kubiak, Laons (FR); Jeremiah Harnett, Gif-sur-Yvette (FR); Nathalie Mondoly, Le Chesnay (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/695,593

(22) PCT Filed: Apr. 29, 2011

(86) PCT No.: PCT/IB2011/001452
§ 371 (c)(1),
(2), (4) Date: Oct. 31, 2012

(87) PCT Pub. No.: WO2011/135461
PCT Pub. Date: Nov. 3, 2011

(65) Prior Publication Data
US 2013/0059016 A1 Mar. 7, 2013

(30) Foreign Application Priority Data
Apr. 29, 2010 (EP) .................................... 10290225

(51) Int. Cl.
*A61K 33/06* (2006.01)
*A61P 1/00* (2006.01)
*A61K 9/10* (2006.01)
*A61K 35/02* (2015.01)
*G01N 17/00* (2006.01)
*A61K 9/00* (2006.01)
*A61K 47/26* (2006.01)
*A61K 47/32* (2006.01)
*A61K 47/38* (2006.01)
*G01N 11/14* (2006.01)

(52) U.S. Cl.
CPC ................. *A61K 9/10* (2013.01); *A61K 35/02* (2013.01); *G01N 17/00* (2013.01); *A61K 9/0095* (2013.01); *A61K 47/26* (2013.01); *A61K 47/32* (2013.01); *A61K 47/38* (2013.01); *G01N 11/14* (2013.01)

(58) Field of Classification Search
None
See application file for complete search history.

(56) References Cited

U.S. PATENT DOCUMENTS

| 2,978,446 | A | | 4/1961 | Battista et al. |
| 3,141,875 | A | | 7/1964 | Battista et al. |
| 4,942,042 | A | * | 7/1990 | Bhargava et al. ............ 424/683 |
| 5,770,217 | A | * | 6/1998 | Kutilek et al. ................ 424/442 |
| 2005/0032905 | A1 | * | 2/2005 | Reo et al. ...................... 514/649 |
| 2007/0231412 | A1 | * | 10/2007 | Hughes et al. ............... 424/683 |
| 2009/0263555 | A1 | * | 10/2009 | Tapfer et al. ................. 426/564 |

FOREIGN PATENT DOCUMENTS

| WO | WO-00-10527 | * | 3/2000 |
| WO | WO-2005-041876 | * | 5/2005 |

OTHER PUBLICATIONS

Guarino et al., "Smectite in the Treatment of Acute Diarrhea: A Nationwide Randomized Controlled Study of the Italian Society of Pediatric Gastroenterology and Hepatology (SIGEP) in Collaboration With Primary Care Pediatricians", Journal of Pediatric Gastroenterology and Nutrition, Jan. 2001, 71-75.*
Smetca, Beaufour-Ipsen Pharma, Dec. 31, 2002, (XP002611476), Retrieved from the Internet: URL:http://www.smecta.md/index.php?domen_id=67&lang=en&sessia=&username_medicina=p. 1, line 1—p. 2, last line.
International Search Report for PCT/IB2011/001452 dated Dec. 23, 2011.
Dioctahedral Smectite Constituent Sheet as referenced in Taiwanese Office Action for Taiwanese Patent Application No. 100114425 dated Nov. 7, 2014.
Taiwanese Office Action for Taiwanese Patent Application No. 100114425 dated Nov. 7, 2014.
W. Leber, *Pharmatherapeutica*, 5:256-60 (1988) (Abstract).
An Introduction to Suspension Concentrates, Vanderbilt Minerals, retrieved Jan. 13, 2016, from the internet at http://www.vanderbiltminerals.com/ee_content/Documents/Technical/Intro_Suspension_Concentrates_Web.pdf.

* cited by examiner

*Primary Examiner* — Jianfeng Song
(74) *Attorney, Agent, or Firm* — Hunton & Williams LLP

(57) ABSTRACT

The present invention relates to liquid or semi-solid pharmaceutical compositions, more specifically to aqueous pharmaceutical suspension or semi-solid paste containing natural mineral clays as active ingredients. These compositions are particularly useful for the treatment of acute and chronic diarrhea.

12 Claims, No Drawings

CLAY COMPOSITIONS

This application is a national stage filing of PCT/IB2011/001452, filed Apr. 29, 2011, which claims priority to EP 10290225.1, filed Apr. 29, 2010, the subject matter of which is incorporated herein in its entirety.

The present invention relates to liquid or semi-solid pharmaceutical compositions, more specifically to aqueous pharmaceutical suspension or semi-solid paste containing natural mineral clays as active ingredient. These compositions are particularly useful for the treatment of acute and chronic diarrhoea.

Natural mineral clays may be chosen from smectite group clays or attapulgite group clays such as attapulgite de Mormoiron. Such clays are useful as active ingredients of pharmaceutical compositions according to the present invention.

A therapeutic composition based on a smectite known as "diosmectite" exists and is sold under the trademark Smecta®. The product sold is dosed in sachets as a powder. The disadvantage of the dry form is the fact that the patient needs to have liquid to prepare the suspension before administration. The homogenization is not necessary easy and active ingredients often remain in the glass which is not convenient. The problem was therefore to develop a novel pharmaceutical composition as a ready-to-use composition wherein all excipients and active substance form a semi-solid or an oral suspension stable over time.

It has been found that the use of a clay, in particular a smectite, in combination with a specific viscosity agent such as, for instance, cellulose derivatives allows to obtain an aqueous suspension, semi-solid or paste, very stable at room temperature. This stable composition presents the advantage of being a ready-to-use composition and as efficient as the compositions of the prior art, while having a pleasant taste and more convenient for uses.

The invention provides stable oral pharmaceutical compositions containing clays as active ingredients and with a determined viscosity which allows to provide pharmaceutical compositions without additional preparation before use, such as dilutions or re-suspension of compounds.

The subject of the present invention is therefore a pharmaceutical composition, as aqueous suspension or semi-solid, and containing a natural clay, preferably a smectite, as the active ingredient, and wherein the viscosity of the pharmaceutical composition is comprised between about 900 mPa·s and 5500 mPa·s (at shear rate 100S-1 for 60 seconds). Such composition allows to provide the pharmaceutical composition as a ready-to-use formulation without additional preparation.

Furthermore, the object of the invention is to provide an ingestible pharmaceutical composition as a suspension or semi-solid paste comprising:
a natural clay, preferably a smectite, as active ingredient,
at least one viscosity agent and
water
wherein the pH of the composition ranges between 2 to 7.5 and the viscosity of the pharmaceutical composition is comprised between about 900 mPas and 5500 mPas.

Furthermore, the object of the invention is to provide an ingestible pharmaceutical composition as a suspension or semi-solid paste comprising
a natural clay, preferably a smectite, as active ingredient,
at least one viscosity agent,
water and,
optionally one ore more constituents selected from preservative, flavouring agent, pH adjuster and a sweetener, and wherein the pH of the composition ranges between 2 to 7.5 and the viscosity of the pharmaceutical composition is comprised between about 900 mPas and 5500 mPas.

Unless otherwise indicated the following definitions are set forth to illustrate and define the meaning and scope of the various terms used to describe the invention herein.

The term "viscosifying agent" or "viscosity agent" as used in the present application refers to excipients used in foods and pharmaceutical compositions as thickeners and are for instance sugar syrup, gum such as xanthane or arabic or agar gum, carbopol polymers, CMC (carboxymethylcellulose), HPC (hydroxypropylcellulose), HEC (hydroxyethylcellulose), HPMC (hydroxypropylmethyecellulose) but not limited to this list.

The term "preservative" as used herein means a pharmaceutically acceptable substance to prevent decomposition by microbial growth or by undesirable chemical change, (i.e. having bactericidal and/or fungicidal or antioxidants properties).

The term "flavour" or "aroma" as used in the present application covers the flavouring ingredients or compositions usually used in the food industry, whether of natural or synthetic origin. It comprises single compounds or mixtures. Specific examples of such compounds can be found in the literature, such as for example in Fenaroli's Handbook of Flavor Ingredients, 1975, CRC Pres or as commercial products.

The term "pH adjuster" as used herein refers to an excipient used in order to adjust the pH at a desired value, such as citric acid or ascorbic acid but not limited to these compounds.

The term "viscosity" is a measure of a fluid's resistance to flow. As viscosity units, P (poise), cP (centi-poise) or Pa·s (pascal second), mPa·s (mili pascal second)—SI unit system—are used. The expression "the viscosity is comprised between about x mPas and y mPas" means a viscosity comprised between (x±3%) mPas and (y±3%) mPas.

Method used for viscosity measurement according to the present invention may be all method known in the art and for instance rotational viscometer. A rotational viscometer measures viscosity by measuring the running torque of the cylindrical rotors immersed in a sample. It is a motorized cylindrical rotor inserted into a sample and rotated at a constant speed. The rotational viscometer employs the measurement method that assumes viscosity is directly proportional to a running torque required to produce a steady rotating motion.

The term "sweetener" refers to a food additive that reproduced the effect of sugar in taste, but usually has less food energy. Some sugar substitutes are natural and some are synthetic.

Unless otherwise stated, all percentages mentioned in the present invention are weight percentages (w/w).

Smectites represent a particular family of clay in which dioctaedral species such as montmorillonite and beidellite, and trioctaedral species such as hectorite and saponite are found.

According to the invention the composition further contains at least a viscosity agent or a mixture thereof. Suitable viscosity agents are for instance carbopol polymers, sugar syrups (glucose, maltitol, xylitol, sorbitol liquid), alginate, gums such as xanthane or arabic or agar gum, or cellulose derivatives, i.e., derivatives commonly known to the skilled person, water insoluble crystalline cellulose or cellulose ethers, such as the crystalline cellulose, methyl, ethyl cellulose, carboxymethylcellulose, hydroxypropylcellulose, hydroxyethylcellulose or hydroxypropylmethylcellulose.

Preferably, the cellulose derivatives are selected from the group consisting of crystalline cellulose, methyl cellulose, ethyl cellulose, carboxymethylcellulose (CMC), hydroxypropylcellulose (HPC), hydroxyethylcellulose (HEC) and the hydroxypropyl methylcellulose (HPMC). Particularly derivatives of cellulose are selected from the group consisting of hydroxypropyl cellulose or those described in U.S. Pat. Nos. 2,978,446 and 3,141,875 (e.g. one of those marketed under the name Avicel®).

A composition according to the present invention may comprise a suitable flavour or a mixture thereof. As a suitable flavour, traditional flavours can be used such as liquorice, exotic fruits, red fruits, extracts of citrus fruits such as lime, lemon, orange, grapefruit, or mandarin oils or coffee, tea, mint, cocoa, vanilla, caramel, chocolate or essential oils. The composition according to the invention may also include encapsulated flavours.

Encapsulated flavour may consist of a flavour into a glassy matrix (encapsulation matrix) made for instance of carbohydrate. Any sugar or sugar derivative that can be processed by extrusion techniques to form a dry extruded solid may be used. Specific examples of suitable components can be selected from the following products: sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysates, maltodextrin but not limited to this list.

A composition may contain a sweetener or a mixture thereof. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, hydrogenated maltose (maltitol) inverted sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Water-soluble sweeteners derived from naturally occurring water-soluble sweeteners, such as a chlorinated derivative of ordinary sugar (sucrose), known, for example, under the product description of sucralose. Suitable sweeteners include also natural sweeteners from plants such as Stevia extract.

A composition according to the present invention may contain one preservative or a mixture thereof. Suitable preservatives include compounds having bactericidal and/or fungicidal or antioxidants properties, such as citric and ascorbic acids, lauryl alcohol, sorbic acid, sodium methyl paraben, sodium propyl paraben, parahydroxymethylbenzoate, parahydroxypropylbenzoate, parahydroxybenzoic acid, potassium sorbate, propylene glycol, chlorhexidine gluconate, bronopol, cetylpyridinium chloride, glycerin (glycerol), alpha tocopherol, butylated hydroxy toluene (BHT).

A composition according to the present invention may contain a pH adjuster or a mixture thereof. Suitable pH adjusters includes natural weak acids such as citric acid, sorbic acid, lactic acids, strong acids, salts thereof and buffers.

According to the invention the natural clay used in a composition according to the present invention is a smectite, and more preferably the smectite used is a dioctahedral smectite. Preferably dioctahedral smectite is a montmorillonite or a beidellite or a crystallographic structure intermediate between the two crystal-chemical structure: montmorillonite and beidellite. This intermediate crystallographic structure can be a montmorillonite structure; it can also be a beidellite structure and very close to the beidellite. Preferably, a smectite according to the invention is a montmorillonite or an intermediate structure close to the montmorillonite, and more preferably very close to the montmorillonite.

In a preferred embodiment, the smectite used is the smectite known as "diosmectite" and used as active substance sold under the trade-mark Smecta®. In a more preferred embodiment, the smectite used in the present composition is smectite known as "diosmectite" within the range between 15% to 40% weight by weight (w/w), and preferably within the range between 20% to 35% (w/w). In a more preferred embodiment the smectite used in the present composition is the smectite known as "diosmectite" within the range between 25% to 35% weight by weight (w/w). In a more preferred embodiment, the clay is the only active ingredient in the composition according to the present invention.

In a preferred embodiment, the composition is as a semi-solid paste. In another embodiment, the composition is as a suspension.

Preferred viscosity agent is selected from sugar syrup (of glucose, maltitol), gum (such as xanthane or arabic or agar gum), carbopol polymers, CMC (carboxymethylcellulose), HPC (hydroxypropylcellulose), HPMC (hydroxypropylmethylcellulose) or a mixture thereof. The viscosity agent of the pharmaceutical composition is present in a concentration range between about 1 and 50% weight by weight (w/w), more preferably between 5 and 40% (w/w).

In a preferred embodiment, the viscosity agent is selected from gum, cellulose derivatives or a mixture thereof, and more particularly from gum such as xanthane gum, cellulose derivatives such CMC (carboxymethylcellulose), HPC (hydroxypropylcellulose), HEC (hydroxyethylcellulose), HPMC (hydroxypropylmethylcellulose) or a mixture thereof.

In a more preferred embodiment, the viscosity agent is selected from xanthane gum, HEC (hydroxyethylcellulose), HPMC (hydroxypropylmethylcellulose) or a mixture thereof.

In a preferred embodiment, the viscosity agent of the pharmaceutical composition the viscosity agent is present in a concentration range between about 0.1 and 5% weight by weight (w/w), more preferably between 0.1 and 2% (w/w).

In a preferred embodiment, the viscosity agent of the pharmaceutical composition is selected from xanthane gum, HEC (hydroxyethylcellulose), HPMC (hydroxypropylmethylcellulose) or a mixture thereof and is present in a concentration range between about 0.1 and 5% weight by weight (w/w), more preferably between 0.1 and 2% (w/w).

In a preferred embodiment, the viscosity agent of the pharmaceutical composition is selected from xanthane gum and is present in a concentration range between about 0.1 and 5% weight by weight (w/w), more preferably between 0.1 and 2% (w/w).

In a preferred embodiment, the viscosity agent of the pharmaceutical composition is selected from HEC (hydroxyethylcellulose), HPMC (hydroxypropylmethylcellulose) or a mixture thereof and is present in a concentration range between about 0.1 and 5% weight by weight (w/w), more preferably between 0.1 and 2% (w/w).

Preferably, the viscosity of the pharmaceutical composition is comprised between about 1100 mPa·s and 3000 mPa·s, and more preferably between 1100 mPa·s and 2500 mPa·s.

In addition the composition according to the invention comprises a preservative or a mixture thereof. More preferably, a composition according to the invention comprises a preservative selected from citric acid, ascorbic acid, sorbic acid, potassium sorbate, propylene glycol and chlorhexidine digluconate. In another preferred embodiment, a composition according to the invention comprises a preservative selected from citric acid, potassium sorbate, ascorbic acid or a mixture thereof. In another preferred embodiment, the preservative is a mixture of citric acid, potassium sorbate and ascorbic acid.

The preservative is preferably present in the composition in a concentration range between 0.01% to 5% weight by weight (w/w), more preferred, in a concentration range between 0.1% to 1% (w/w).

Preferably, when the preservative used in the pharmaceutical composition is potassium sorbate the pH should be lower than pH 6 in order to produce an antimicrobial effect.

As preferred embodiment, a composition according to the present invention comprises a flavour or a mixture thereof. As preferred embodiment, a composition according to the present invention comprises, as flavour, natural extracts, essential oils or a mixture thereof. The flavours are preferably chosen from the traditional flavours such as liquorice, exotic fruits, red fruits, extracts of citrus fruits, vanilla, caramel and chocolate.

Preferably, a composition according to the invention comprises at least one flavour chosen from vanilla, chocolate and/or caramel. Preferably, the flavour is in a concentration range between 0.2% to 3% weight by weight (w/w), preferably between 0.5% to 2% (w/w).

More preferred flavour or aroma is caramel/cacao flavour in a concentration range between 0.2. % to 3% weight by weight (w/w), preferably between 0.5% to 1.5% (w/w).

The flavour can be mixed with solvents, adjuvant, additives and/or other substances, for example those usually used in the flavour and/or food industry.

Preferably, composition according to the invention comprises a sweetener or a mixture thereof. More preferably, the composition contains an artificial sweetener. According to the invention preferable sweeteners are water-soluble artificial sweeteners which include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Water-soluble sweeteners derived from naturally occurring water-soluble sweeteners, such as a chlorinated derivative of ordinary sugar (sucrose), known, for example, under the product description of sucralose. Natural sweeteners from plants such as Stevia extract may also be used.

More preferably, the sweetener is selected from sodium saccharin.

More preferably, the sweetener is selected from sodium saccharin, sucralose, a natural sweetener from plants extract or a mixture thereof.

In a further preferred embodiment, the sweetener is present in the composition in a concentration range between 0.02% to 0.5% weight by weight (w/w), preferably between 0.03% to 0.3% (w/w).

As preferred embodiment, the composition according to the invention encompasses a pH adjuster. Preferably the pH adjuster is selected from natural weak acids such as citric acid, sorbic acid, lactic acids, strong acids, salts thereof and buffers. More preferably the pH adjuster is a natural weak acids. Even more preferably the pH adjuster is selected from citric acid and sorbic acid.

More preferably the pH range used is between 2 and 7.5, preferably between 4 to 6.

More preferably the pH range used is between 2 and 7.5, preferably between 4.3 to 7.

In a preferred embodiment, a composition according to the invention contains a natural clay, preferably smectite, as active ingredient within the range of between 20% to 35% (w/w), a viscosity agent in a concentration the range of 5% to 40% (w/w), a preservative in a concentration range of 0.1% to 1% (w/w), a pH adjuster for a pH range of 4 to 6, a flavour in a concentration range of 0.5 to 1.5% (w/w), a sweetener in a concentration range of 0.04% to 0.3% (w/w) and finally completed to the desired weight with purified water.

In a preferred embodiment, a composition according to the invention contains a natural clay, preferably smectite, as active ingredient within the range of between 20% to 35% (w/w), a viscosity agent in a concentration the range of 0.1% to 2% (w/w), a preservative in a concentration range of 0.1% to 1% (w/w), a pH adjuster for a pH range of 4.3 to 7, a flavour in a concentration range of 0.5 to 1.5% (w/w), a sweetener in a concentration range of 0.03% to 0.3% (w/w) and finally completed to the desired weight with purified water.

As further object, the invention also encompasses a process for the preparation of an oral liquid suspension or semi-solid paste, comprising the steps of:
  weighing the components
  dissolution of compounds pH adjuster if any(s), preservative if any at room temperature under stirring
  addition of the viscosity agent, flavour and sweetening agent under stirring
  addition of the clay such as smectite All components were weighed. Thereafter, the pH adjuster(s) were dissolved in water at room temperature. The preservative was dissolved in water at room temperature Thereafter, to the remaining quantity of water under agitation was added the viscosity agent, the artificial flavoring agent and the sweetening agent.

Preferably, pH adjuster(s) such as ascorbic/citric acid solution was added to the latter solution under agitation and the resulting solution transferred to an appropriate reactor known to the skilled person in this field. Suitable reactor is for example a blade-paddle homogenizer reactor.

The natural clay such as for instance smectite is optionally sieved before use and is added to the reactor portion wise. Stirring is continued to homogenize the mixture. When the smectite is added to water an exothermic reaction often evolved.

In addition, increase of temperature influences the viscosity therefore the smectite is added portion-wise to control or eliminate heat evolution thus controlling viscosity of final suspension.

Finally, the preservative solution is introduced into the reactor and optionally stirred to homogenize. After duration time of about 15 minutes of agitation the expected product composition is obtained as creamy suspension. The temperature of the suspension is optionally followed by the presence of an internal temperature probe and the reactor temperature is optionally controlled via a cooling thermostatic apparatus habitually used in this field.

Temperature is set at a temperature ranges between 15 and 30° C. preferably at a temperature of 25° C.

Furthermore, agitation speed of the reactor is preferably between about 700 rpm and 1500 rpm, preferably at a speed of about 1200 rpm. Agitation time is about 15 minutes. Type of agitator is for instance a blade-paddles system.

Optionally, a step of micronisation of the smectite used can be carried out before the implementation of the method described above. The micronization may be performed eg using a conventional milling.

Micronization, besides a positive impact on the stability of the suspension, also has the advantage of diminishing the unpleasant effect formed by the sandy texture of the suspension.

According to another embodiment of the invention and the manufacturing process described above, all intermediate solutions of excipients may be prepared by increasing or controlling the temperature if required. For instance for dissolution of the components.

As mentioned previously, to remove the unpleasant taste of the smectite, it is possible to add to the suspension of smectite solution comprising a sweetening agent. The sweetening agent may include sucrose, glucose, hydrogenated glucose, maltitol, sorbitol, Preferably, the sweetener will be used in any proportion.

In addition, it is also possible to add an artificial flavour commonly used, including an aroma of vanilla, strawberry, raspberry, lemon, chocolate, coffee, etc. Preferably, the artificial flavor is selected from the group consisting of artificial vanilla flavour, the artificial orange/vanilla flavour and artificial caramel/cacao flavour.

The daily administration dose is the usual recommended dose for this product. In the particular case of the smectite known as "diosmectite" can be administered at a maximum daily dose of 18 g/day.

Preferably, the compositions according to the invention provide an immediate delivery of therapeutic dose of 3 g of smectite.

Compositions according to the present invention can be used for the prevention and/or treatment of certain pathologies such as the symptomatic treatment of pain associated of acute and chronic diarrhoea, pains associated with oesogastroduodenal, colonic diseases and coeliac disease in adults and children.

Furthermore, valuable advantages presented by such compositions is an easy use, no reconstitution step and preparation before use and no dose adjustment of the active substance.

Preferably, the composition according to the invention is a ready to use suspension form with acceptable taste and texture, preferably packaged in a sachet, a tubular sachet, bottle made of various materials conventionally used for such packaging.

Various techniques such as radiosterilisation or autoclave sterilisation could be used for semi-solid formulation/paste as disclosed in the invention to obtain an aseptic preparation.

Unless otherwise indicated, all technical and scientific terms used herein have the same meaning as commonly understood by a specialist ordinary domain associated with this invention. Similarly, all publications, patent applications, all patents and other references mentioned herein are incorporated by reference.

The following examples are presented to illustrate the above procedures and should not be considered as limiting the scope of the invention.

EXPERIMENTAL PART

Viscosity Method and Parameters

Sample suspensions were prepared for analysis. These samples were kept relaxed during 24 hours at 5° C. before being analysed. The viscosity of samples was measured at 25.0° C.±0.1° C., at 100 s$^{-1}$ using the viscosimeter RheolabQC with the measuring cylinder CC27. Table 1 summarize the equipment and conditions used for the measurement of the viscosity.

TABLE 1

| Equipment | Viscosimeter RheolabQC + geometry CC27 |
|---|---|
| Measuring temperature | 25° C. |
| Relaxation time | 24 hours |
| Parameters | 1) Thermal Equilibrium Time: 30 minutes |
| | 2) Pre-Shearing at 100 s$^{-1}$, 30 seconds, 5 measuring points |
| | 3) Shearing at 100 s$^{-1}$, 60 seconds, 20 measuring points |
| Viscosity expressed as | The average of 20 measuring points |
| Units | m.Pa.s |

Example 1

The following example was prepared on kilo scale.

Ascorbic acid (2.00 g) (to adjust pH) and citric acid (4.00 g) (to adjust pH) were dissolved in water at room temperature (200 ml). The preservative, potassium sorbate, was dissolved in water at room temperature (200 ml). Thereafter, to the remaining quantity of water under agitation was added the viscosity agent (500 g, maltitol liquid), the artificial flavouring agent (10 g of Aroma caramel/Cacao 22P294) and the sweetening agent (1.2 g of saccharin sodium). The ascorbic/citric acid solution was added to the latter solution under agitation and the resulting solution transferred to an appropriate reactor.

The appropriate amount of diosmectite (previously sieved before use through a 1 mm sieve) was added to a blade-paddle homogenizer reactor portion wise. Stirring was continued to homogenize the mixture.

Finally, the preservative solution was introduced into the reactor and stirred to homogenize. After 15 minutes of agitation 2 kilos of the expected product was obtained as a light creamy colored suspension.

The temperature of the suspension was followed by the presence of an internal temperature probe and the reactor temperature was controlled via a cooling thermostatic apparatus. Temperature was set at 25° C. Agitation speed of reactor was 1200 tr/min. Agitation time was 15 minutes. Type of agitator was blade-paddles.

The composition thus obtained is as follows:

| Composition per sachet | Amounts used per sachet |
|---|---|
| Diosmectite | 3 g |
| | (30%) |
| Maltitol liquid | 2.5 g |
| | (25%) |
| Sodium saccharin | 0.006 g |
| | (0.06%) |
| Aroma caramel/Cacao 22P294 | 0.005 g |
| | (0.5%) |
| Potassium Sorbate | 0.0175 g |
| | (0.175%) |

-continued

| | |
|---|---|
| Ascorbic acid | 0.010 g (0.10%) |
| Citric acid | 0.02 g (0.2%) |
| Purified Water | 4.3965 g |

| Parameters | Results |
|---|---|
| Viscosity (mPa.S) | 1893 mPa.s at 100 s−1 |
| pH | 5.08 |

Example 2

Compositions with Various Viscosity Agents 2.1. Composition with Maltitol as Viscosity Agent
2.1.1 Preparation of the Compositions The viscosity agent (maltitol liquid) was dissolved in water at room temperature under agitation and the resulting solution transferred to an appropriate reactor (for example a blade-paddle homogenizer reactor). The appropriate amount of smectite (previously sieved before use through a 1 mm sieve) was added to the beaker (using a laboratory mechanical stirrer) portion wise. Stirring was continued to homogenize. After 5 minutes of agitation 700 g of the expected product was obtained as a light creamy coloured suspension.

2.1.2 Results

TABLE 2

| Formula | 2 | 3 | 4 | 5 |
|---|---|---|---|---|
| smectite | 210 g | 210 g | 210 g | 210.0 g |
| Maltitol liquid | 210 g (30%) | 175.0 g (25%) | 140 g (20%) | 105.0 g (15%) |
| Purified water | 280 g | 315 g | 350.0 g | 385 g |
| Viscosity (mPa s) | 1925 at 100 s$^{-1}$ | 1840 at 100 s$^{-1}$ | 1498 at 100 s$^{-1}$ | 1107 at 100 s$^{-1}$ |

2.2. Composition with Maltitol and Hydroxyl Propyl Cellulose (HPC) as Viscosity Agent
2.2.1 Preparation of the Compositions The HPC viscosity agent was dissolved in 100 ml water at room temperature. To the remaining quantity of water under stirring was added 210 g of a solution of maltitol as viscosity agent The appropriate amount of diosmectite (previously sieved before use through a 1 mm sieve) was added to the beaker (using overhead laboratory mechanical stirrer) portion wise. Stirring was continued to homogenize.

Finally, the preservative solution was introduced into the beaker (using overhead laboratory mechanical stirrer) and stirred to homogenize.

After 5 minutes of agitation 700 g of the expected product was obtained as a light creamy coloured suspension.

2.2.2 Results

TABLE 3

| Formula | 6 | 7 | 8 |
|---|---|---|---|
| smectite | 210 g | 210 g | 210 g |
| Maltitol liquid | 210 g | 210 g | 210 g |
| HPC | 1.05 g (0.15%) | 3.50 g (0.5%) | 7.00 g (1.0%) |
| Purified water | 278.95 g | 276.5 g | 273.03 g |

TABLE 3-continued

| Formula | 6 | 7 | 8 |
|---|---|---|---|
| Viscosity (mPa s) | 1951 at 100 s$^{-1}$ 984 at 300 s$^{-1}$ | 1237 at 100 s$^{-1}$ 590 at 300 s$^{-1}$ | — 673 at 300 s$^{-1}$ |

2.3. Composition with Maltitol and CMC as Viscosity Agents
2.3.1 Preparation of the Compositions The compositions are prepared according to the manufacturing process as described under example 2.2.1.

2.3.2 Results

TABLE 4

| Formula | 9 | 10 | 11 |
|---|---|---|---|
| Diosmectite | 210.0 g | 210.0 g | 210.0 g |
| Maltitol liquid | 210.0 g | 210.0 g | 105.0 g |
| CMC | 1.05 g (0.15%) | 0.70 g (0.1%) | 0.21 g (0.03%) |
| Purified water | 278.95 g | 279.3 g | 384.79 g |
| Viscosity (mPa s) | Thick Paste not tasted. | 6473 at 100 s−1 | 2504 at 100 s−1 |

2.4. Composition with Maltitol and Carbapol-974P as Viscosity Agents
2.4.1 Preparation of the Compositions The compositions are prepared according to the manufacturing process as described under example 2.2.1.

2.4.2 Results

TABLE 5

| Formula | 12 | 13 |
|---|---|---|
| Diosmectite | 210.0 g | 210.0 g |
| Maltitol liquid | 105.0 g | 105.0 g |
| Carbapol-974P | 0.70 g (0.1%) | 0.56 g (0.08%) |
| Purified water | 384.30 g | 384.44 g |
| Viscosity (mPa s) | 2626 at 100 s−1 | 2326 at 100 s−1 |

Example 3

Compositions with Various Amounts of Maltitol 3.1. Preparation of the Compositions Different compositions were prepared under with different amounts of maltitol according to the following process.

The viscosity agent (Maltitol liquid) was dissolved in water at room temperature under agitation and the resulting solution transferred to an appropriate reactor (for example a blade-paddle homogenizer reactor). The sweetening agent (1.5 g) was added to the latter solution under agitation. An artificial flavoring agent (7.5 g) was added to the latter solution under agitation. The appropriate amount of Diosmectite (previously sieved before use through a 1 mm sieve) was added to the reactor portion wise. Stirring was continued to homogenize. After 15 minutes of agitation 2.5 kilos of the expected product were obtained as a light creamy colored suspension.

3.2. Results

TABLE 6a

| formula | 19 | 20 | 21 | 22 |
|---|---|---|---|---|
| Diosmectite | 450.00 g | 450.00 g | 450.00 g | 450.00 g |
| Maltitol liquid | 75.00 g (5%) | 150.00 g (10%) | 225.00 g (15%) | 300.00 g (20%) |
| Saccharin sodium | 1.50 g | 1.50 g | 1.50 g | 1.50 g |
| Aroma caramel/ Cacao 22P294 | 7.50 g | 7.50 g | 7.50 g | 7.50 g |
| Purified water | 966.00 g | 891.00 g | 816.00 g | 741.00 g |
| pH | 7.20 | 7.11 | 7.10 | 7.32 |
| Viscosity (mPa.s) | 1185 | 1061 | 1343 | 1782 |

TABLE 6b

| formula | 23 | 24 | 25 | 26 |
|---|---|---|---|---|
| Diosmectite | 450.00 g | 450.00 g | 450.00 g | 450.00 g |
| Maltitol liquid | 375.00 g (25%) | 450.00 g (30%) | 600.00 g (40%) | 750.00 g (50%) |
| Saccharin sodium | 1.50 g | 1.50 g | 1.50 g | 1.50 g |
| Aroma caramel/ Cacao 22P294 | 7.50 g | 7.50 g | 7.50 g | 7.50 g |
| Purified water | 666.00 g | 591.00 g | 441.00 g | 291.00 g |
| pH | 7.30 | 7.36 | 7.41 | 7.48 |
| Viscosity (mPa.s) | 2045 | 2474 | 2970 | 4913 |

Example 4

Composition with Antimicrobial Agent (or Preservative)

4.1. Preparation of the Compositions

The acid was dissolved in water at room temperature. (100 ml). The preservative (potassium sorbate) was dissolved in water room temperature (100 ml).

To the remaining quantity of water under agitation was added the viscosity agent and maltitol liquid. The sweetening agent was added to the latter solution under agitation and the resulting solution transferred to an appropriate reactor (for example a blade-paddle homogenizer reactor). Acid solution was added to the latter solution under agitation and the resulting solution transferred to an appropriate reactor. The artificial flavoring agent was added to the latter solution under agitation and the resulting solution transferred to an appropriate reactor. The appropriate amount of diosmectite (previously sieved before use through a 1 mm sieve) was added to the reactor portion wise. Stirring was continued to homogenize. The preservative solution was added to the suspension under agitation to an appropriate reactor.

After 15 minutes of agitation 2.5 kilos of the expected product were obtained as a light creamy colored suspension.

4.2 Results

TABLE 7a

| formula | 28 | 29 | 30 | 31 |
|---|---|---|---|---|
| Diosmectite | 450.00 g | 450.00 g | 450.00 g | 450.00 g |
| Maltitol liquid-Lycasin 80/55 | 450.00 g | 450.00 g | 450.00 g | 450.00 g |
| Saccharin sodium | 1.500 g | 1.500 g | 1.500 g | 1.500 g |
| Aroma caramel/ Cacao 22P294 | 7.500 g | 7.500 g | 7.500 g | 7.500 g |
| Sorbic acid | 3.000 g (0.20%) | 3.000 g (0.20%) | — | 3.000 g (0.20%) |
| Citric acid | — | 30.00 g (2.0%) | 30.00 g (2.00%) | — |
| Ascorbic acid | — | 1.500 g (0.10%) | 1.500 g (0.10%) | — |
| Potassium sorbate | — | — | 3.000 g (0.2%) | — |
| Propylene Glycol | — | — | — | 22.00 g (15.0%) |
| Chlorhexidine Digluconate 20% | — | — | — | — |
| Purified water | 588.00 g | 556.50 g | 556.50 g | 588.00 g |
| pH | 5.22 | 2.51 | 2.67 | 5.48 |
| Microbiological Challenge Test | Compliant | Compliant | Compliant | Compliant |

TABLE 7b

| formula | 32 | 33 | 34 | 35 |
|---|---|---|---|---|
| Diosmectite | 450.00 g | 600.00 g | 600.00 g | 600.00 g |
| Maltitol liquid-Lycasin 80/55 | 450.00 g | 600.00 g | 600.00 g | 600.00 g |
| Saccharin sodium | 1.500 g | 2.00 g | 2.00 g | 2.00 g |
| Aroma caramel/ Cacao 22P294 | 7.500 g | 10.00 g | 10.00 g | 10.00 g |
| Sorbic acid | 3.000 g (0.20%) | — | — | — |
| Citric acid | — | — | 10.00 g (0.50%) | 20.00 g (1.00%) |
| Ascorbic acid | — | — | — | — |
| Potassium sorbate | — | 2.00 g (0.10%) | 4.00 g (0.20%) | 4.00 g (0.20%) |
| Propylene Glycol | — | — | — | — |
| Chlorhexidine Digluconate 20% | 0.750 g (0.01%) | — | — | — |
| Purified water | 587.25 g | 786.00 g | 774.00 g | 764.00 g |
| pH | 5.25 | 7.00 | 3.89 | 3.19 |
| Microbiological Challenge Test | Compliant | Not compliant | Compliant | Compliant |

All compositions are conform/compliant. No increase in microbial population was observed between T14 days and T28 days. Tests performed according to Pharmacopoeia §5.1.3.

Example 5

The compositions summarized in table 8 are prepared according to the manufacturing process as described under example 2.2.1 (all the amounts are expressed in % (w/w).

TABLE 8

| formula | 36 | 37 | 38 | 39 |
|---|---|---|---|---|
| Diosmectite | 30 | 30 | 30 | 30 |
| HEC | — | — | 1.5 | 1.7 |
| Xanthan gum | 0.3 | 0.25 | — | — |
| Aroma caramel/Cacao 22P294 | 1 | 1 | 1 | 1 |
| Sucralose | 0.0375 | 0.0375 | 0.0375 | 0.0375 |
| Potassium sorbate | 0.175 | 0.175 | 0.175 | — |
| Ascorbic acid | 0.1 | 0.1 | 0.1 | 0.1 |
| Citric acid | 0.2 | 0.2 | 0.2 | 0.2 |
| Purified water | qs to 100% | qs to 100% | qs to 100% | qs to 100% |
| pH | 4.8 < pH < 6.5 | 4.8 < pH < 6.5 | 4.8 < pH < 6.5 | 4.8 < pH < 6.5 |
| viscosity | 1300 < mPas < 2500 | 1300 < mPas < 2500 | 1300 < mPas < 2500 | 1300 < mPas < 2500 |

Example 6

Stability Study

After 3 months of storage at 25° C./60%RH no significant change of the drug product quality attributes has been reported. The composition (of example 1) remains within the proposed shelf-life specifications.

Accelerated Storage Conditions (40° C./75% RH)

After 3 months of storage at 40° C./75% RH no significant change of the drug product quality attributes has been reported, with the exception of the potassium sorbate content which decreases slightly (−3.6%). The composition (of example 1—Batch P60146.01) remains within the proposed shelf-life specifications.

The stability results are summarized in tables 9 (Stability Testing Protocol Storage Conditions and Sampling Times) and 10 (summary of stability results)

TABLE 9

| | Sampling time (months) | | | |
|---|---|---|---|---|
| Storage conditions | 0 | 1 m | 3 m | 6 m |
| 25° C. ± 2° C./60% RH ± 5% RH | a, b, c, d | | a, c | a |
| 40° C. ± 2° C./75% RH ± 5% RH | a, b, c, d | a | a, c | a, c, d | a-General characteristics, pH, adsoptive capacity, diosmectite assay, potassium sorbate assay
b-uniformity of content, potassium sorbate identification
c-microbiological quality
d-efficacy of antimicrobial preservation

TABLE 10

| | | Time Point (Months) | | |
|---|---|---|---|---|
| Test | Shelf life Specification | 0 | 1 m | 3 m |
| GENERAL CHARACTERISTICS | Sachet containing a light beige and homogenous suspension having a reminiscent odour of caramel | Complies | Complies | Complies |
| TESTS | | | | |
| pH | 4.0 to 6.0 | 4.9 | 5.0 | 5.0 |
| Adsorptive capacity (with washing) | 0.3 to 0.5 g/g | 0.5 | 0.5 | 0.5 |
| Adsorptive capacity (without washing) | 0.3 to 0.5 g/g | N.A. | N.A. | 0.5 |
| Viscosity | 900-2500 mPa.s | 1721 | 1849 | 1882 |
| ASSAY | | | | |
| Diosmectite | 2.70 to 3.30 g per theorical sachet (3.00 g ± 10%) | 3.06 | 3.05 | 3.06 |
| Potassium sorbate | 14.0-19.3 mg per theorical sachet (17.5 mg/unit −20%, +10%) | 16.9 | 16.6 | 16.3 |
| MICROBIOLOGICAL TESTS | | | | |
| Total aerobic microbial count | ≤100 CFU/g | <5 CFU/g | NA | <5 CFU/g |
| Total combined yeast and moulds | ≤10 CFU/g | <5 CFU/g | NA | <5 CFU/g |
| *Escherichia coli* | Absence/1 g | Absence | NA | Absence |
| Challenge test | Complies | Complies | NA | |

The invention claimed is:

1. A pharmaceutical composition comprising:
   (i) 30% to 35% by weight (w/w) natural dioctahedral smectite as the only active ingredient;
   (ii) about 0.1% to about 5% by weight (w/w) xanthan gum;
   (iii) a pH adjuster;
   (iv) 0.01% to 5% by weight (w/w) preservative selected from citric acid, potassium sorbate, ascorbic acid, and mixtures thereof;
   (v) 0.5% to 2% by weight (w/w) flavoring agent;
   (vi) about 0.02% to 0.5% by weight (w/w) sweetener selected from sodium saccharin, sucralose, a natural sweetener from plant extract, and mixtures thereof; and
   (vii) water;
   wherein the pH of the composition is between 4 and 6, the composition has a viscosity of between about 1100 mPa·s and about 2500 mPa·s, and the composition is an aqueous suspension or in a semi-solid state.

2. A pharmaceutical composition comprising:
   (i) 30% to 40% by weight (w/w) natural dioctahedral smectite as the only active ingredient;
   (ii) about 0.1% to about 5% by weight (w/w) xanthan gum;
   (iii) a pH adjuster;
   (iv) 0.01% to 5% by weight (w/w) preservative selected from citric acid, potassium sorbate, ascorbic acid, and mixtures thereof;
   (v) 0.5% to 2% by weight (w/w) flavoring agent;
   (vi) about 0.02% to 0.5% by weight (w/w) sweetener selected from sodium saccharin, sucralose, a natural sweetener from plant extract, and mixtures thereof; and
   (vii) water;
   wherein the pH of the composition is between 4 and 6, the composition has a viscosity of between about 1100 mPa·s and 2500 mPa·s, and the composition is an aqueous suspension or in a semi-solid state.

3. The pharmaceutical composition according to claim 2, wherein: xanthan gum is present in an amount of from 0.1% to 2% by weight (w/w); the preservative is present in an amount of from 0.1% to 1% by weight (w/w); the pH adjuster is present in an amount that adjusts the composition to a pH of from 4 to 6; the flavoring agent is present in an amount of from 0.5% to 1.5% by weight (w/w); and the sweetner is present in an amount of from 0.03% to 0.3% by weight (w/w).

4. The pharmaceutical composition according to claim 2, wherein xanthan gum is present in an amount of from about 0.1 to about 2% by weight (w/w).

5. The pharmaceutical composition according to claim 2, wherein the preservative is present in an amount of from about 0.1 to about 1% by weight (w/w).

6. The pharmaceutical composition according to claim 2, wherein the sweetener is present in an amount of from about 0.03% to about 0.3% by weight (w/w).

7. The pharmaceutical composition according to claim 2, wherein the flavoring agent is present in an amount of from 0.5% to 1.5% by weight (w/w) and provides a caramel/cacao flavor.

8. The pharmaceutical composition according to claim 2, wherein the viscosity is between about 1300 mPa·s and about 2500 mPa·s.

9. The pharmaceutical composition according to claim 2, which is a ready-to-use formulation.

10. The pharmaceutical composition according to claim 2, which is a ready-to-use formulation in a sachet.

11. The pharmaceutical composition according to claim 2, which is a ready-to-use formulation in a tubular sachet.

12. The pharmaceutical composition according to claim 2, wherein the dioctahedral smectite is sieved.

* * * * *